United States Patent
Akioka et al.

(10) Patent No.: US 6,464,940 B1
(45) Date of Patent: Oct. 15, 2002

(54) PH SENSOR AND PH MEASUREMENT METHOD EMPLOYING THE SAME

(75) Inventors: Koji Akioka, Amagasaki; Akira Sanjoh, Nara, both of (JP)

(73) Assignee: Sumitomo Metal Industries, Ltd., Osaka (JP)

( * ) Notice: Subject to any disclaimer, the term of this patent is extended or adjusted under 35 U.S.C. 154(b) by 0 days.

(21) Appl. No.: 09/592,722

(22) Filed: Jun. 13, 2000

(30) Foreign Application Priority Data

Jun. 14, 1999 (JP) .......................................... 11-167110

(51) Int. Cl.$^7$ .............................................. G01N 27/00
(52) U.S. Cl. .................... 422/82.01; 204/433; 204/416; 204/422; 205/789; 205/787.5; 422/68.1
(58) Field of Search ................................ 422/88, 82.01; 204/433, 416, 419; 428/701; 257/252, 253; 205/789, 787.5

(56) References Cited

U.S. PATENT DOCUMENTS

| | | | | |
|---|---|---|---|---|
| 3,905,889 A | * | 9/1975 | Macur et al. ............. | 204/195 P |
| 4,028,196 A | * | 6/1977 | Young ....................... | 205/787.5 |
| 5,221,456 A | * | 6/1993 | Benton et al. ............... | 204/416 |
| 5,319,226 A | * | 6/1994 | Sohn et al. .................. | 257/253 |
| 5,376,255 A | * | 12/1994 | Gumbrecht et al. ........ | 204/426 |
| 5,387,328 A | * | 2/1995 | Sohn .......................... | 204/403 |
| 5,414,284 A | * | 5/1995 | Baxter et al. ................ | 257/253 |
| 5,814,280 A | * | 9/1998 | Tomita et al. ............ | 422/82.01 |
| 5,833,824 A | * | 11/1998 | Benton ........................ | 204/416 |
| 5,892,252 A | * | 4/1999 | Hammond et al. .......... | 257/252 |
| 5,911,873 A | * | 6/1999 | McCarron et al. .......... | 205/789 |
| 5,918,110 A | * | 6/1999 | Abraham-Fuchs et al. .... | 438/48 |
| 6,132,893 A | * | 10/2000 | Schoning et al. ........... | 428/701 |
| 6,236,075 B1 | * | 5/2001 | Hsiung et al. .............. | 257/252 |

FOREIGN PATENT DOCUMENTS

| | | |
|---|---|---|
| JP | 1152355 | 6/1989 |
| JP | 1291152 | 11/1989 |
| JP | 2031149 | 2/1990 |
| JP | 2223854 | 9/1990 |
| JP | 7167821 | 7/1995 |
| JP | 10153575 | 6/1998 |

OTHER PUBLICATIONS

Basic Properties of the Electrolyte-SiO$_2$-Si System: Physical and Theoretical Aspects—IEEE Transactions on Electron Devices, vol. ED-26, No. 11, Nov. 1979 pp. 1805-1815.

* cited by examiner

Primary Examiner—Jill Warden
Assistant Examiner—Brian Sines
(74) Attorney, Agent, or Firm—Barnes & Thornburg

(57) ABSTRACT

A pH sensor is provided capable of readily determining the pH of a solution of a small amount. The pH sensor includes a semiconductor substrate, an oxide film provided on the semiconductor substrate, a solution storage part for holding a solution on the oxide film, and an electrode to be in contact with the solution in a vicinity of the oxide film. To determine the pH of a solution, a capacitance-voltage characteristic is initially monitored by the sensor between the electrode in contact with the solution and another electrode provided on the back surface of the semiconductor. Then the pH of the solution is derived from a flat band voltage which is obtained based on the capacitance-voltage characteristic.

4 Claims, 6 Drawing Sheets

PH SENSOR AND PH MEASUREMENT METHOD EMPLOYING THE SAME

BACKGROUND OF THE INVENTION

1. Field of the Invention

The present invention relates to pH sensors and pH measurement methods, and in particular to pH sensors and pH measurement methods suitable for measuring the pHs of solutions of small amounts.

2. Description of the Background Art

A conventional sensor for measuring the pH of a solution employs an ion-sensitive field effect transistor (ISFET). This sensor includes an ISFET 201 and a reference electrode 202, as shown in FIG. 10. To measure the pH of a solution 203, ISFET 201 and reference electrode 202 are placed in sample solution 203. The gate potential of ISFET 201 varies with the pH of solution 203, and such variation is used to measure the pH of the solution. In this conventional technique, however, an ISFET and a reference electrode both must be placed in a solution and for a small amount of solution its pH can hardly be measured.

SUMMARY OF THE INVENTION

An object of the present invention is to provide a pH sensor capable of readily measuring the pH of a solution of a small amount.

Another object of the present invention is to provide a pH sensor having a simple structure applicable to biosensors and the like.

According to the present invention, a pH sensor is provided which includes a semiconductor substrate, an insulating film provided on the semiconductor substrate, a solution storage part provided to hold a solution on the insulating film, and a metal electrode provided to be in contact with the solution.

According to the present invention, the solution storage part may have a surrounding wall provided to hold a solution on the insulating film.

According to the present invention, a pH measurement method is provided in which a solution is introduced into the solution storage part of the pH sensor of the present invention as described above, and then a capacitance-voltage characteristic is determined between the metal electrode in contact with the solution and a surface of the substrate forming the sensor which is opposite to the substrate surface having the insulating film provided thereon. A flat band voltage is obtained based on the determination, and the pH of the solution is obtained based on the flat band voltage.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
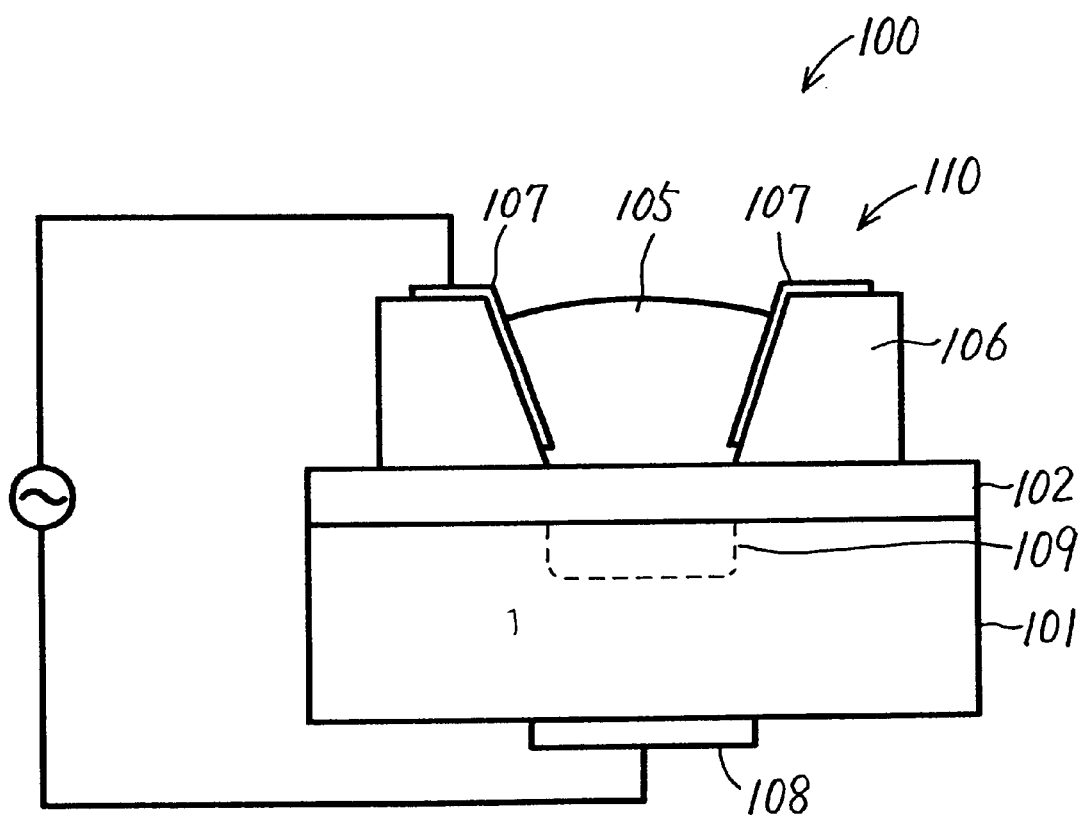
FIG. 1 is a schematic cross section of a pH sensor according to the present invention.

In an embodiment of the present invention, a pH sensor is configured as shown in FIG. 1. A pH sensor 100 has an n-type silicon substrate 101 and a $SiO_2$ film 102 formed on substrate 101. On substrate 101 is provided a solution storage part 110 which is composed of $SiO_2$ film 102 and a surrounding wall 106 damming the flow of a solution 105. A metal electrode 107 is provided on surrounding wall 106 and it is extended in the direction of $SiO_2$ film 102 to come in contact with the solution held in solution storage part 110. Silicon substrate 101 has a back surface (that is opposite to the substrate surface having $SiO_2$ film 102 thereon) provided with a terminal electrode 108.

When an inorganic oxide is placed in a aqueous solution, its surface is hydrated to produce hydroxyl groups, which dissociate to give electric charge on the oxide surface. Thus a surface potential is generated on the oxide surface depending on the pH of the solution. The oxide surface can be positively charged at a low pH by addition of protons, while it can be negatively charged at a high pH by elimination of protons from OH groups. Generally, oxides have a point at which an apparent potential of zero is achieved, i.e., isoelectric point, and they can have a negative surface potential at a higher pH than such point and a positive surface potential at a lower pH than such point. For example, $SiO_2$ can dissociate as follows to have surface potentials varying with pH.

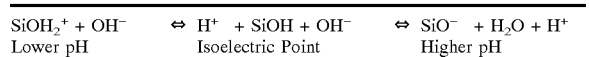

| $SiOH_2^+$ + $OH^-$ | ⇔ $H^+$ + SiOH + $OH^-$ | ⇔ $SiO^-$ + $H_2O$ + $H^+$ |
|---|---|---|
| Lower pH | Isoelectric Point | Higher pH |

Other oxides can have surface potentials caused by similar mechanisms and their isoelectric points and potential values can differ from each other depending on their type. For example, $SiO_2$ has an isoelectric point of approximately 1.8 to 2.8. Although the mechanism cannot be shown in detail, a nitride surface can also have a electric potential generated in an aqueous solution depending on the pH of the solution. For example, $Si_3N_4$ whose isoelectric point is approximately four to five can have a positive surface potential at a lower pH and a negative surface potential at a higher pH than the isoelectric point. Thus, nitride film such as $Si_3N_4$ film may be used as the insulating film in place of $SiO_2$ film.

Figure 2:
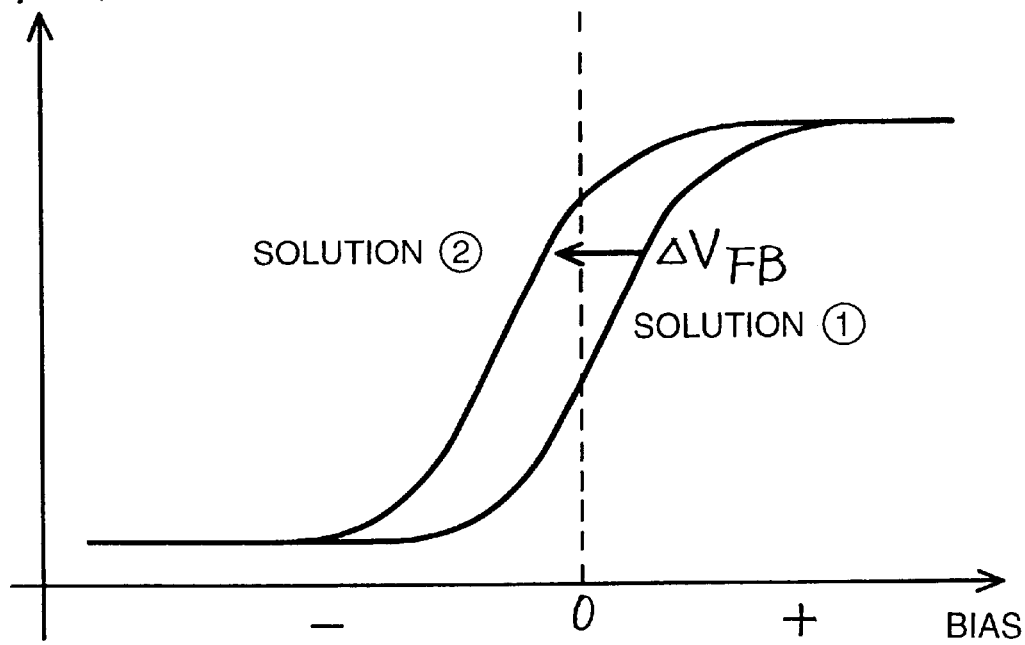
FIG. 2 represents a capacitance-voltage characteristic determined with the pH sensor shown in FIG. 1.

When the sensor 100 shown in FIG. 1 receives an aqueous solution in solution storage part 110 with $SiO_2$ film 102 exposed, an electric potential is generated on the surface of $SiO_2$ film 102 depending on the pH of the solution. The carrier concentration of the silicon substrate surface provided with the insulating film is changed in response to the electric potential. A change is also produced in the capacitance of a depletion layer 109 formed in silicon substrate 101 at a portion close to solution 105 (or the depletion layer changes in thickness). Thus, in sensor 100 having an MOS or MIS structure, a capacitance-voltage characteristic (a high frequency characteristic) between metal electrode 107 and terminal electrode 108 varies depending on the pH of solution 105. Such variation is shown in FIG. 2. The figure represents capacitance-voltage characteristics for two types of solutions having different pHs. As shown in FIG. 2, capacitance-voltage characteristic can shift in the direction of the Voltage axis depending on pH.

Figure 3:
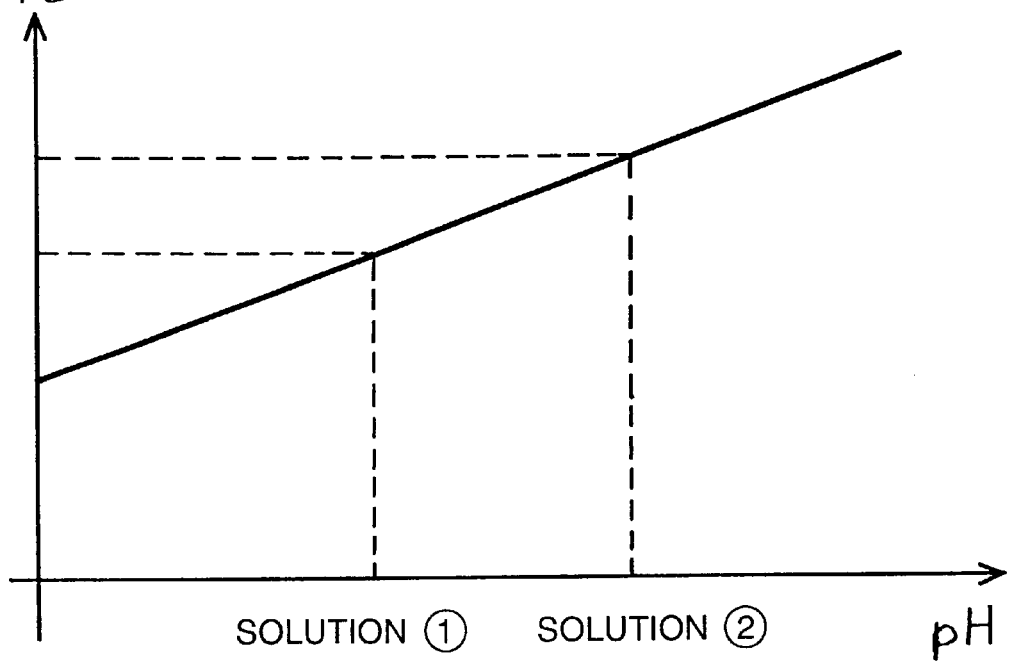
FIG. 3 is a graph showing the relation between the pH of solution and the flat band value obtained from the capacitance-voltage characteristic determined with the pH sensor shown in FIG. 1.

In advance, different capacitance-voltage characteristics of various solutions having their pHs previously known can be obtained by using the pH measurement apparatus as shown in FIG. 1 with a measuring frequency of approximately 1 MHz applied, so that a correlation between pH values and flat band voltages ($V_{FB}$) can be obtained. Typically, pH values can be correlated with flat band voltages ($V_{FB}$) as shown in FIG. 3. Such correlation can be used to obtain the pH of an unknown solution. In a specific manner, pH sensor 100 is connected to a C-V meter and C-V recorder. Then a solution for determination is introduced into solution storage part 110 and a C-V characteristic is determined between electrodes 107 and 108 to obtain a $V_{FB}$. From the obtained $V_{FB}$ and a previously obtained correlation between pH values and flat band voltages ($V_{FB}$), such as shown in FIG. 3, the pH of the solution of interest can be determined.

The present pH sensor has a significantly simple structure (a MOS or MIS structure) and therefore it can readily be fabricated by conventional semiconductor device manufacturing process techniques, such as lithography, chemical vapor deposition and etching. The solution storage part of the sensor can receive a drop of a solution from a pipette or the like to determine the pH of the solution of as small an amount as several $\mu$l to several tens $\mu$l. The sensor may be fabricated on a silicon substrate and thus be fabricated together with other semiconductor sensors or semiconductor biosensors on a single substrate. Furthermore, such sensors can be linked together via a solution channel which can readily be formed by etching the substrate or the like. Thus a semiconductor device can be provided which has multiple functions including the pH measurement function on a single chip. Such a device can be useful in the field of biotechnology.

In the pH sensor as described above, the n-type Si substrate may be replaced with a p-type Si substrate or other types of semiconductor substrates including a Ge substrate and a compound semiconductor substrate such as a GaAs substrate. In addition, the $SiO_2$ film may be replaced with other types of oxide film, such as $Al_2O_3$ film and $TiO_2$ film, or replaced with nitride film such as $Si_3N_4$. The insulating film typically has a thickness of 100 Å to 1 $\mu$m, preferably of 500 Å to 3000 Å. The electrode may be formed of Pt, Pd, Au or the like.

EXAMPLE

Figure 4:
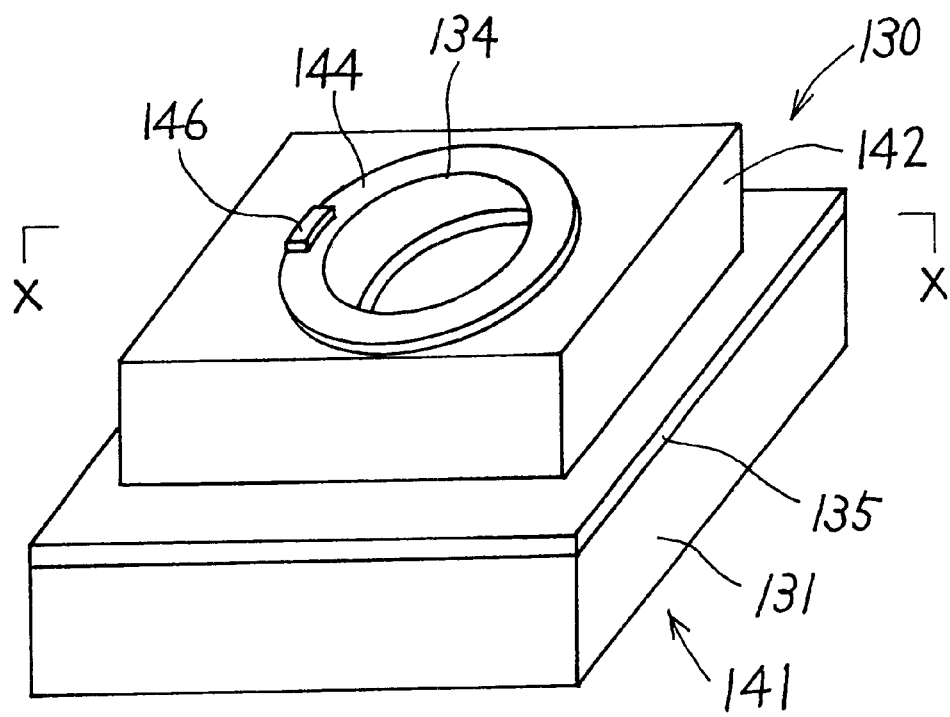
FIG. 4 is a perspective view showing another pH sensor according to the present invention.
Figure 5:
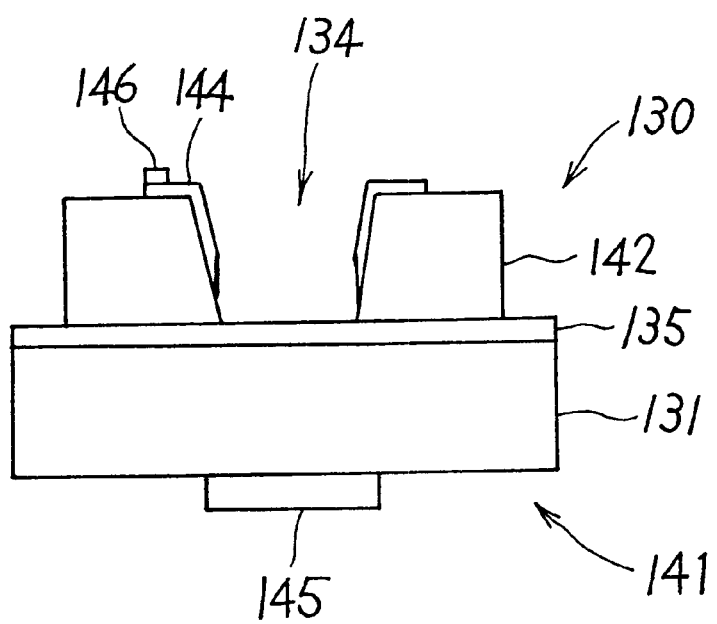
FIG. 5 is a cross section of the sensor shown in FIG. 4.

A pH sensor was fabricated as shown in FIGS. 4 and 5. The pH sensor 130 has a base part 141 including a silicon substrate 131, and a solution holding plate (a surrounding wall) 142 formed of Pyrex glass and joined thereto. The base part 141 has a size of 7 mm×7 mm. The base part 141 and the plate 142 together form a pH monitoring cell 134. The plate 142 has a size of 6 mm×6 mm and a height of 0.5 mm. The silicon substrate 131 has a surface covered with a silicon oxide film 135 of approximately 200 nm in thickness. The cell 134 is a cylinder or circular truncated cone of approximately 4 mm in diameter. The cell's size may be varied depending on the purpose.

Figure 6:
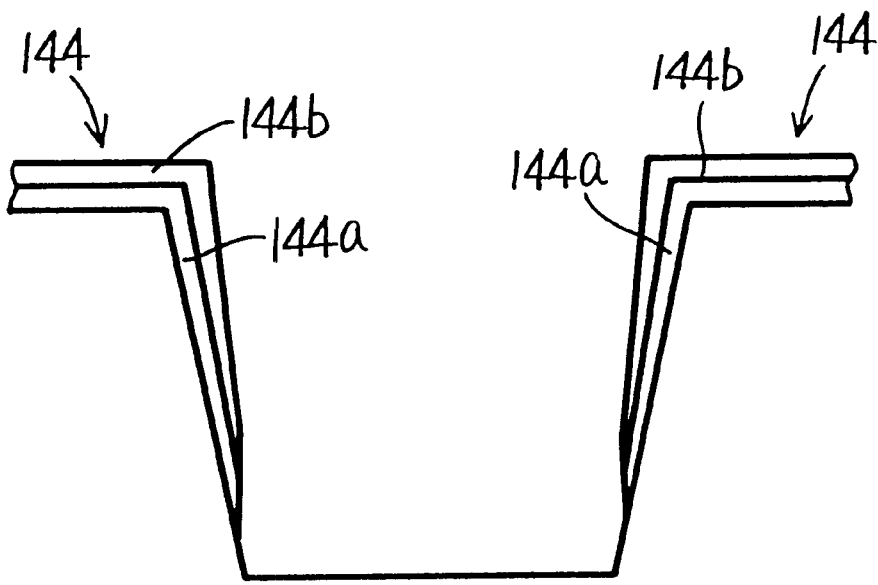
FIG. 6 is an enlarged cross section showing the electrode of the sensor shown in FIG. 4.

An electrode 144 is provided on the plate 142 forming the cell 134, and an electrode 145 is also provided on a back surface of the silicon substrate 131. As shown in FIG. 6, the electrode 144 has a two-layered structure formed of a Ti layer 144a and a Pt layer 144b. The underlying Ti layer 144a is provided to enhance the contact with the Pyrex glass. On the electrode 144 a terminal 146 is provided. The silicon substrate 131, the silicon oxide film 135, and the electrodes 144 and 145 constitute a pH sensor unit.

Figure 7A:
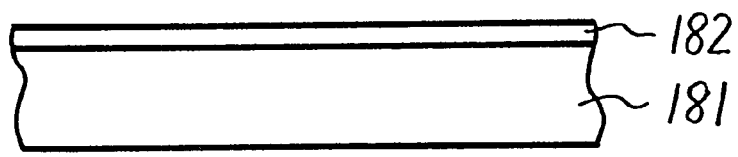
FIGS. 7A and 7B are schematic cross sections illustrating a process for fabricating the base part of the sensor shown in FIG. 4.
Figure 7B:
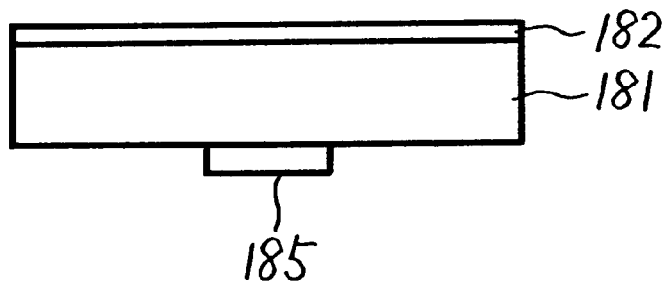

The base part of the apparatus shown in FIG. 4 can be mass-produced at a time on a silicon wafer by a common semiconductor device manufacturing process. For example, as shown in FIG. 7A, initially a silicon wafer 181 is thermally oxidized to provide in a surface thereof a silicon oxide film 182 of approximately 200 nm in thickness. Then the silicon wafer is cut off or scribed to provide chips, which are then provided with an electrode 185 to give a large number of base parts (FIG. 7B).

Figure 8A:
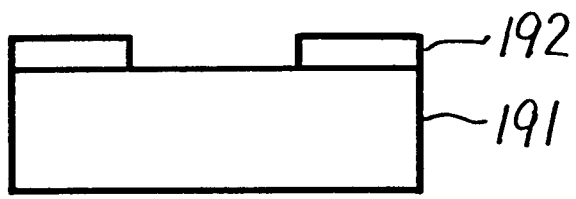
FIGS. 8A–8F are schematic cross sections illustrating a process for fabricating a solution holding plate of the sensor shown in FIG. 4.
Figure 8B:
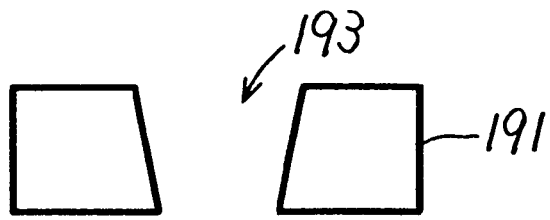
Figure 8C:
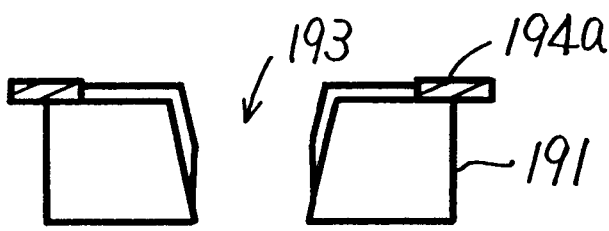
Figure 8D:
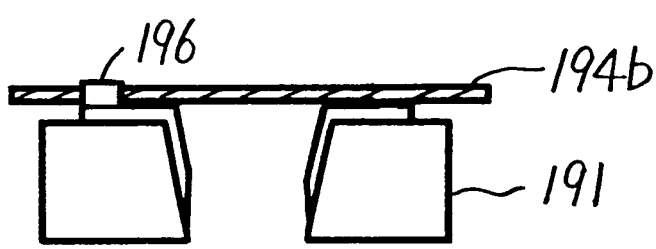
Figure 8E:
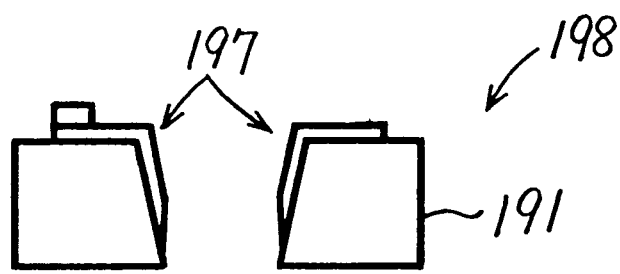
Figure 8F:
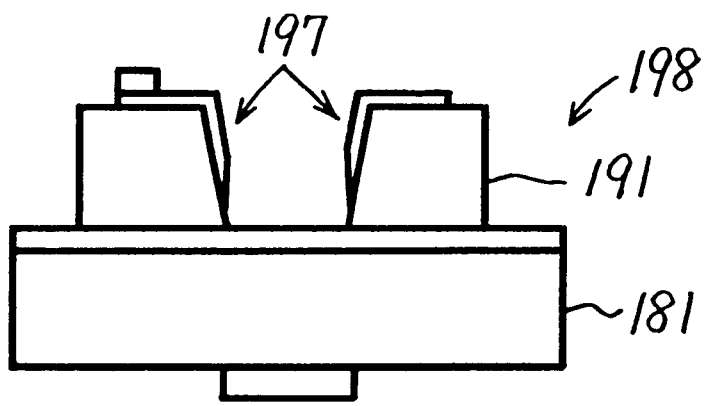

The solution holding plate may also be formed by common etching and sputtering techniques, as for example shown in FIGS. 8A to 8F. Initially, as shown in FIG. 8A, on a surface of a Pyrex glass plate 191 a resist mask 192 is provided in a predetermined pattern. Then, the glass plate 191 is wet-etched with hydrofluoric acid or diamond-blasted to provide a throughhole 193 therethough (FIG. 8B). Then, with a hard mask 194a of SUS plate covering portions other than the throughhole 193 which will form a pH monitoring cell, sputtering is carried out to provide a Ti/Pt film 195 (FIG. 8C). Then, with a hard mask 194b covering a desired portion, sputtering is carried out to provide an Au terminal 196 for connection (FIG. 8D). Thus a solution holding plate 198 is obtained which has an electrode portion 197 as shown in FIG. 8E. The obtained plate is typically joined by anodic bonding to the base part obtained by the process shown in FIGS. 7A and 7B, to give the apparatus shown in FIG. 4 (FIG. 8F).

Figure 9:
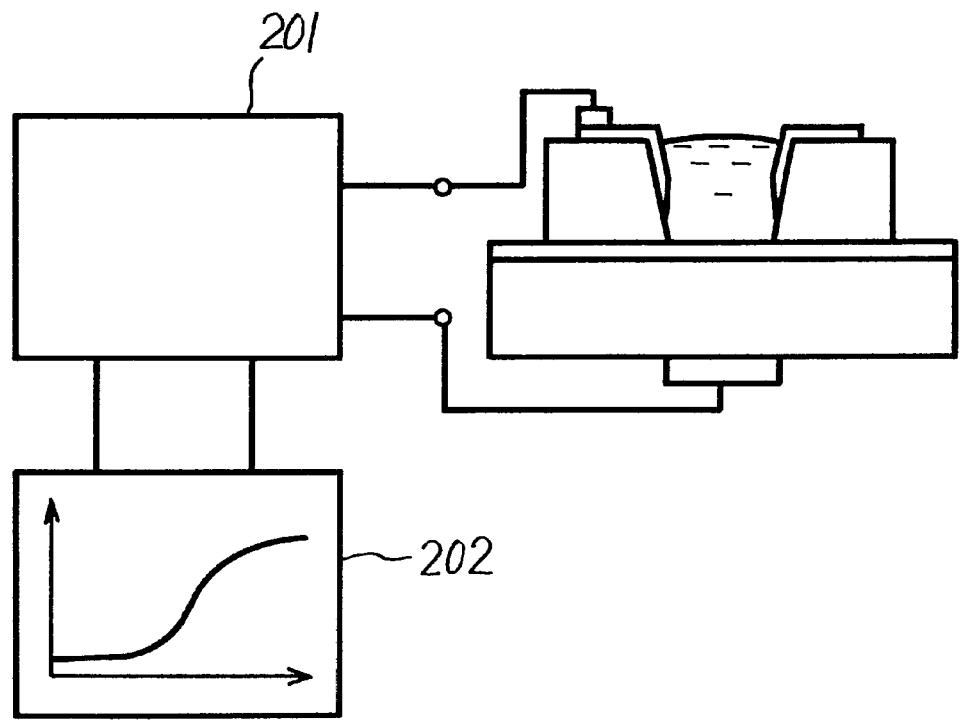
FIG. 9 is a schematic view for illustrating a pH measurement flow with the sensor shown in the FIG. 4.
Figure 10:
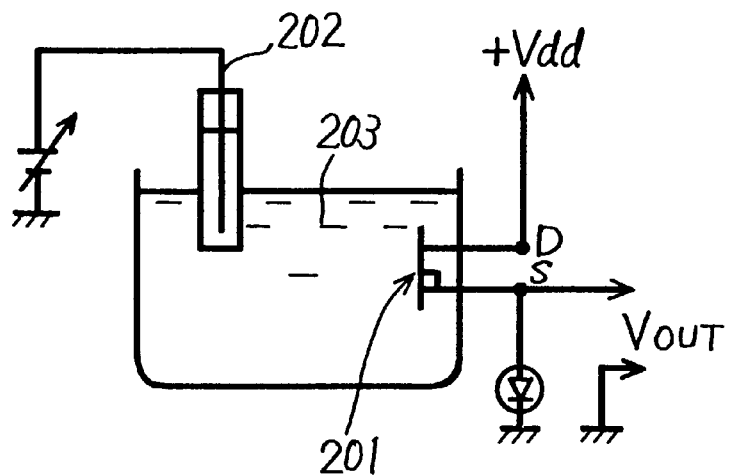
FIG. 10 is a schematic view of a conventional pH sensor.

By the apparatus shown in FIG. 4, pH is determined as described below. As shown in FIG. 9, the electrode of the pH monitoring cell is connected to a C-V meter 201 to which an X-Y recorder 202 is connected. Then a solution is dropped onto the pH monitoring cell and a C-V characteristic is determined. The obtained C-V characteristic is used to obtain a $V_{FB}$. The pH of the solution is derived from the obtained $V_{FB}$ and a previously obtained correlation between pH values and $V_{FB}$s.

A 1-chip multifunctional device with multiple sensors and solution channels may be provided which is equipped with a pH sensor of the present invention as a part. For example, a device of 10 mm in width and 50 mm in length may have a pH sensor having an opening of approximately 3 mm in diameter at a certain portion thereof.

Thus the present invention provides an apparatus which can determine pHs in a simple structure with a small amount of solution. The apparatus according to the present invention can be formed on a semiconductor substrate and therefore be fabricated together with other devices on a single substrate. The apparatus according to the present invention may also be a monolithic device having a pH measurement function as well as other functions. The present invention may be used in various areas, such as analytic chemistry and medical services, for determining pHs with a small amount of various solutions. The device of the present invention is also applicable to biosensors.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pH sensor for determining a pH of a solution, comprising:
    a semiconductor substrate;
    an insulating film on said semiconductor substrate;
    a surrounding wall on said insulating film forming a solution storage part with the insulating film; and
    an electrode on said surrounding wall for contacting solution in the solution storage part.

2. The pH sensor of claim 1, including a terminal electrode on a surface of said semiconductor substrate which is opposite to the semiconductor surface having said insulating film provided thereon for determining a capacitance-voltage characteristic between said metal electrode and said terminal electrode.

3. A pH sensor for determining a pH of a solution, comprising:
    a semiconductor substrate;
    an insulating film on said semiconductor substrate;
    a glass plate having a throughhole forming a surrounding wall on said insulating film; and
    an electrode on said surrounding wall for contacting solution in the throughhole.

4. The pH sensor of claim 3, wherein said semiconductor substrates is a silicon substrate, and said silicon substrate and said glass plate are joined to each other via said insulating film.

* * * * *